United States Patent [19]

Jensen

[11] Patent Number: 4,663,087
[45] Date of Patent: May 5, 1987

[54] METHOD OF COMMINUTING FROZEN ANIMAL ORGANS OR FROZEN ANIMAL TISSUE

[75] Inventor: Willy H. Jensen, Madrid, Spain

[73] Assignee: Laboratorios Leo S.A., Madrid, Spain

[21] Appl. No.: 753,489

[22] Filed: Jul. 10, 1985

Related U.S. Application Data

[63] Continuation of Ser. No. 573,269, Jan. 23, 1984, abandoned, which is a continuation of Ser. No. 441,127, Nov. 12, 1982, abandoned, which is a continuation of Ser. No. 201,103, Oct. 28, 1980, abandoned, which is a continuation of Ser. No. 782,260, Mar. 25, 1977, abandoned, which is a continuation of Ser. No. 596,131, Jul. 15, 1975, abandoned.

[30] Foreign Application Priority Data

Jul. 8, 1974 [GB] United Kingdom ............... 31903/74

[51] Int. Cl.$^4$ ........................ A61K 37/26; C07K 7/40
[52] U.S. Cl. ..................................... 530/305; 424/95; 424/104; 424/106; 424/110; 424/111
[58] Field of Search ................. 424/95, 104, 106, 110, 424/111; 260/112.7; 514/3

[56] References Cited

U.S. PATENT DOCUMENTS

| | | | |
|---|---|---|---|
| 2,637,680 | 5/1953 | Petersen | 260/112.7 |
| 2,695,861 | 11/1954 | Maxwell et al. | 260/112.7 |
| 2,779,706 | 1/1957 | Homan | 260/112.7 |
| 3,297,533 | 1/1967 | Szent-Gyorgyi et al. | 260/112.7 |
| 3,720,657 | 3/1973 | De Vries | 260/112.7 |

*Primary Examiner*—Frederick E. Waddell
*Attorney, Agent, or Firm*—Beveridge, DeGrandi & Weilacher

[57] ABSTRACT

A method of comminuting frozen blocks of animal organs or animal tissue, such as for example pancreas glands, lungs, liver, thyroid glands and intestinal mucosa, from which hormones and other physiologically active substances are to be extracted. The blocks are comminuted by a chip-forming treatment whereby they are transformed into a snow-like mass having an extremely large surface. For the said comminution a machine of the planing machine type can e.g. be used.

10 Claims, 1 Drawing Figure

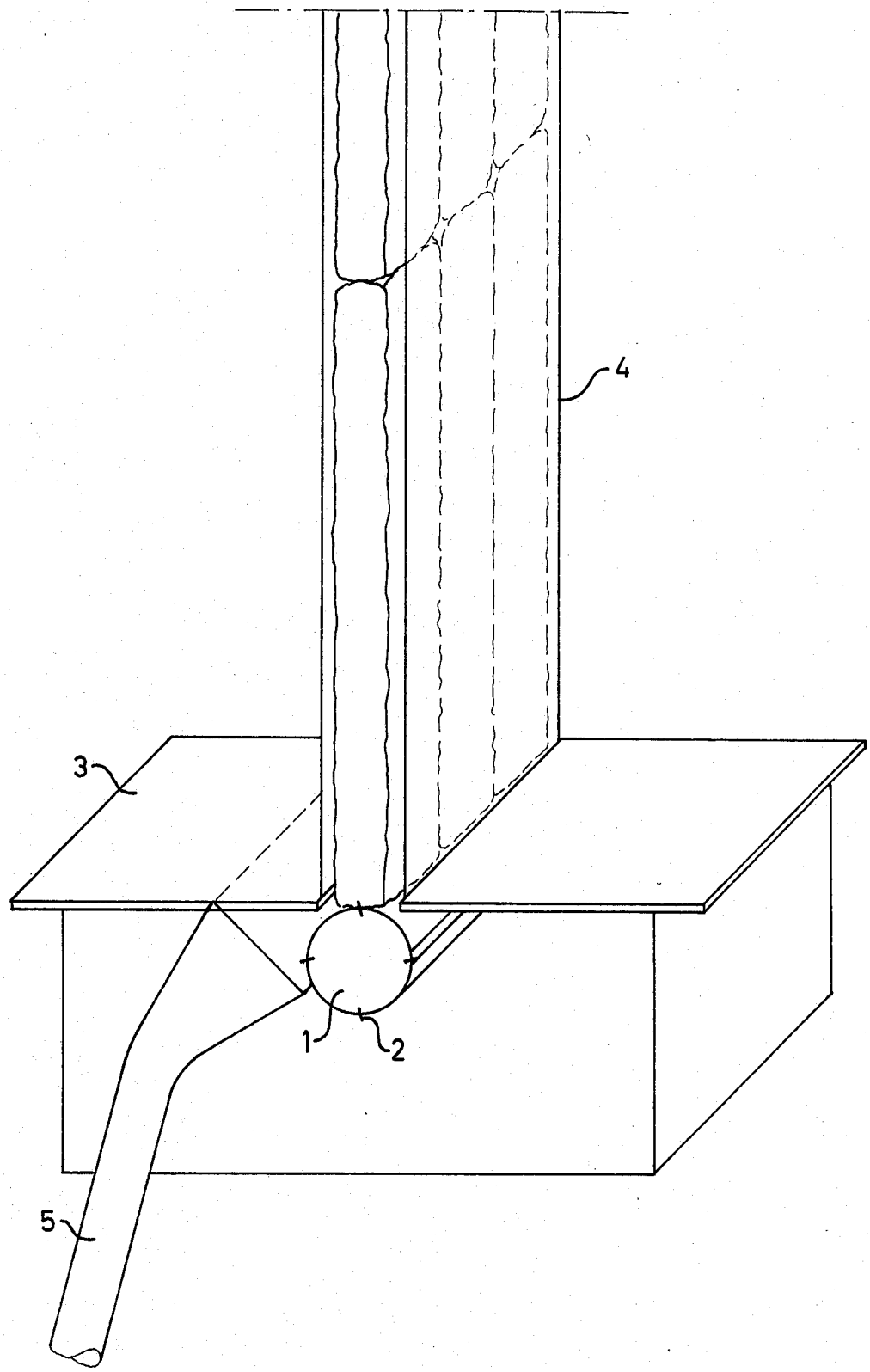

METHOD OF COMMINUTING FROZEN ANIMAL ORGANS OR FROZEN ANIMAL TISSUE

This application is a continuation of application Ser. No. 573,269, filed Jan. 23, 1984, and now abandoned, which was a continuation of application Ser. No. 441,127, filed Nov. 12, 1982, and now abandoned, which was a continuation of application Ser. No. 201,103, filed Oct. 28, 1980, and now abandoned, which was a continuation of application Ser. No. 782,260, filed Mar. 25, 1977, and now abandoned, which was a continuation of application Ser. No. 596,131, filed July 15, 1975, and now abandoned.

BACKGROUND OF THE INVENTION

The invention relates to a method of comminuting frozen animal organs or frozen animal tissue, from which physiologically active substances or other valuable substances are to be extracted.

For the production of such substances from animal organs or animal tissue the factories usually receive the raw material in frozen state, e.g. in the form of frozen blocks.

Before they can be used for the extraction of the desired substance or substances such frozen raw materials have to be comminuted, a process which previously has been carried out by chopping or cutting or in any similar manner resulting in rather coarse lumps or in slices which can be compared to slices of rolled meat sausage.

As examples of such raw materials mention can be made of pancreas glands for the production of insulin, which are supplied to the insulin factories from the slaughter-houses in the form of frozen blocks having for instance the shape and size of a large flat loaf. These blocks are stored, until they are to be used, in cold store, e.g. at $-15°$ C.

Furthermore, mention can be made of lungs, liver, thyroid glands and intestinal mucosa, e.g. from cows, calves, sheep and pigs, from which heparin and other hromones, enzymes and other valuable substances can be extracted.

The recovery of these substances takes place in general by extraction. The necessary extraction time and the yield obtained by the extraction depend, inter alia, on the fineness and the consistency of the raw material after its comminution; the material obtained by the hitherto used comminuting methods has not given particularly satisfactory results in these respects.

In case of the preparation of insulin from pancreas glands, the frozen blocks have, prior to the extraction normally effected with acidified diluted alcohol, been comminuted by chopping or cutting. The machines most commonly used for comminution have been mincing machines or machines with a rotary shaft to which are fitted radially three or four arms provided with knives cutting up the block in slices similar to those cut from a rolled meat sausage. The chopping results in a material similar to minced meat from an ordinary industrial meat mincing machine; this material has as a consequence of the compression during the chopping a comparatively high weight in relation to its volume. By the cutting one obtains slices 2–5 mm thick and of an area of for instance 10×6 cm or 15×12 cm.

For obtaining a reasonable yield of proteins, and thereby of insulin, the total extraction of the pancreas glands comminuted as aforementioned requires a comparatively long time, being of the order of 6 hours, which partly delays the production, partly involves a loss of insulin because this, as long as it is in solution in the extraction medium, is exposed to the decomposing effect of different substances, such as fatty acids and enzymes, even though it is intended to inactivate the latter by the alcohol added.

Notwithstanding the deficiency of the extraction stage, the said cutting or chopping or methods equivalent to these have been used ever since the production of insulin had its beginning almost half a century ago.

SUMMARY OF THE INVENTION

The invention now relates to a process affording a marked reduction of the extraction period in the extraction from comminuted animal organs and comminuted animal tissue and at the same time an increase in the yield of the extracted amount of valuable substance such as insulin and other hormones and enzymes.

According to the invention the frozen animal organs or the frozen animal tissue are subjected to a chip-forming treatment whereby they are transformed into a snow-like mass, e.g. by being treated in a machine of the planing machine type used by joinery factories for the planing of boards.

BRIEF DESCRIPTION OF THE DRAWINGS

The FIGURE is a simplified representation of the use of a planing machine.

DETAILED DESCRIPTION

The comminution results in the production of chips or flakes similar to snow flakes or very fine shavings. Out of regard to the extraction time and yield it is preferable that the thickness of the chips does not exceed for instance about 0.3 mm and preferably does not exceed for instance 0.1 mm. It can suitably be for instance 0.05–0.1 mm. The length of the produced chips is usually between about 0.5 and about 3 mm. In one embodiment chips are formed with a thickness of the order of 0.05–0.3 mm and a length of the order of 0.5–3 mm and in another embodiment chips are formed with a thickness of about 0.05–0.1 mm and a length of about 0.5–2 mm. But the object of the invention, viz. reduction of the extraction time and increase in the extraction yield, can also be achieved with chips of other dimensions than the ones just mentioned, the decisive point being only that the chips are of such a thickness and extent that they form together a light and porous snow-like mass.

The chips formed by the chip-forming treatment will as a result of their small thickness be easily broken into still smaller chips or small particles, e.g. just as a result of the air resistance or as a result of collision with the walls of the apparatus when they are ejected from the comminuting member.

They form as aforementioned a snow-like mass, thus a voluminous mass having a very low weight in relation to its volume, which is in contrast to the very compact mass obtained by comminuting in a mincing machine.

The invention will in the following be explained in more detail, taking the production of insulin as an example.

The frozen blocks of pancreas glands are subjected to the said chip-forming treatment, whereby they are transformed into a snow-like mass having an extremely large surface—probably 1000–10000 times larger than the surface of the glands chopped or cut in the known manner.

The "snow" is thrown or blown from the machine into a funnel or tube and can be conveyed from there direct to the extraction vat.

The extraction can, e.g. be carried out along the conventional method with acidified 80% ethanol, whereby use may be made of twice as much 80% ethanol in liters as the amount of pancreas in kilos.

Due to the enormous surface of the comminuted, disintegrated glands, the extraction can be carried out most rapidly, say in by far less than half the time consumed for the conventional extraction. At the same time the yield increases, partly due to the improved extraction, partly on account of the shorter period during which the extracted insulin contained in the solution is exposed to the decomposing effect of enzymes and other foreign substances.

To this comes that the extraction mass consisting of a liquid phase, viz. ethanol, water and acid, e.g. hydrochloric acid, sulphuric acid or phosphoric acid, with extracted dissolved material, and solid pancreas matter, due to the comminution forms a more homogenous mass than the mass obtained by the conventional comminution, viz. chopping or coarse cutting, and extraction. The pancreas particles comminuted according to the invention and being consequently much lighter in weight remain for a much longer time dispersed in the liquid medium than the former coarsely cut pancreas parts. The conveyance through pumps as well as for instance into filter presses proceeds much more easily and without obstruction, as there will be no long shreds or fibres of pancreas.

The separation of solid pancreas matter and extraction fluid can be effected in a well-known manner, say by centrifugation, filtration or pressing.

EXAMPLE

Frozen blocks of pig's pancreas having the dimensions 60×15×5 cm and weighing approximately 6 kg each are comminuted in a planing machine, a sketch of which is shown on the drawing, in isometric view, partly in section. The drawing does not show driving mechanisms, bearings etc. of the planing machine, as these parts of the machine can be construed in a completely conventional manner.

The machine has a cylinder 1, approximately 50 cm long and 10 cm in diameter, which is mounted with two ball bearings. Four knives 2 of the same length as the cylinder are clamped each in one of four grooves milled longitudinally in the cylinder, not radially, but inclined into the cylinder. The knives project from the circumference of the cylinder, and the height of the projection can be adjusted according to the desired thickness of chip. The cylinder with its bearings and knives is built into a two-piece table 3 of stainless steel the two parts of which are separated by a split above the cylinder. The cylinder is driven by an electromotor causing it to run at a speed of 4000–6000 r.p.m. Above the cylinder and fitted to the table is a high funnel 4 of rectangular cross section with vertical sides into which the frozen blocks of pancreas glands are placed in upright position, three beside each other. The sides of the funnel are so high that several blocks can be placed on top of each other. The 3 bottom blocks rest on the cylinder by their own weight and move constantly downwards, as do the superposed blocks, gradually as the knives of the cylinder strip off the pancreas matter in the form of tiny chips. The thickness of the chips produced depends on the height of the projection of the knives on the cylinder and, furthermore, on the pressure exerted on the cylinder by the stack of blocks. This pressure can, if desired, be increased by means of a pressure-exerting member acting upon the uppermost surface of the stack. Due to the high-speed rotation of the cylinder, the chips are drawn down under the table top and thrown in one and the same direction out of the machine and into a tube 5 from which they can be conveyed direct to the extraction vat. The high velocity at which the chips, being as thin as tissue paper, are flung out from the machine involves that they are further disintegrated into the finest small particles, partly due to the air resistance, partly due to the clash with the tube wall.

By using a speed of 5000 r.p.m. it is possible, with the machine described above, to cup up three blocks of the type mentioned in the course of few minutes, depending on the adjusted thickness of chip, it will be appropriate to set the thickness of chip on approximately 0.05–0.1 mm. A mass is obtained hereby which has an extremely large surface area and is as light and porous as newly fallen snow in frosty weather.

The comminution of the frozen pancreas glands can be effected at normal room temperature, in which case the disintegrated "pancreas snow" should be conveyed as rapidly as possible to the extraction vat, as it will otherwise thaw out quickly and form a slimy mass which is more difficult to handle.

It will be an advantage to comminute the glands at a temperature slightly below zero, e.g. from $-1°$ to $-5°$ C.

The machine requires very little space, as the table need only be so large that the feed funnel can be clamped on same, and the feeding can be made automatically, which is recommendable if the machine is to be installed in cold stores.

In the case described above the bottom blocks rest directly on the cylinder.

The apparatus can, by simple modifications, be adapted for use also in connection with blocks the smallest dimension of which is larger than the diameter of the cylinder. In such case the funnel is placed movably on the table, in such a manner that it can be given a reciprocating movement transversely to the axis of the cylinder. With a view to the comminuting of blocks which rest on the two-piece table during the treatment it is expedient that the table can be raised and lowered so that the thickness of chip also can be adjusted in this manner, i.e. without the knives having to be displaced.

The extraction is effected with acidified 80% ethanol (temperature 8°–12° C.). It may possibly be carried out in several steps. A total extraction of e.g. 200 kg "pancreas snow" takes 90 minutes. The extraction mass is a very uniform mass with little tendency to depositing the finely disintegrated pancreas matter. It contains no long fibres or shreds of pancreas and therefore gives no trouble in transport.

The entire extraction mass is filtered with formation of a solid mass and a yellowish, clear, raw extract.

The extracted amount of insulin from for instance pig's pancreas is 5000–6000 I.U. per kg pancreas in the raw extract. Normally the conventional extraction with an extraction period of the order of 4–6 hours yields max. 3300–3500 I.U. insulin per kg pancreas in the raw extract.

The extract is processed in any convenient manner to pure insulin.

In the comminution of other glands than pancreas glands and other animal material, such as thyroid glands, lungs, liver and intestinal mucosa, one proceeds in a manner similar to the one described above, a snow-like mass being produced, which presents a very large surface for the extraction.

The comminuted materials are processed in any convenient manner to the desired substance or substances.

What we claim is:

1. A method for comminuting a frozen block of pancreas glands from which insulin is recovered by extraction, said method comprising coverting said frozen block into a mass of chips, said mass being as light and porous as newly fallen snow in frosty weather, by comminuting said frozen block in a machine that simultaneously forms chips of the frozen glands from said frozen block and throws said chips away from said frozen block, said communition being carried out under such conditions that formed chips do not thaw out before they reach the extraction vat, and extracting said chips, said extraction being carried out in one or several steps and the total extraction time being of the order of 90 minutes.

2. Method according to claim 1 in which the throwing of said chips results in a reduction in size of said chips.

3. Method according to claim 1 in which the chips when thrown away from the frozen block collide with the walls of said machine or clash with the wall of a tube for conveying the chips to the extraction vat whereby said chips are broken into smaller chips or small particles.

4. Method according to claim 1 in which said frozen block is comminuted in a machine of the planing machine type.

5. Method according to claim 1 wherein said chips are formed with a thickness of the order of 0.05-0.3 mm and a length of the order of 0.5-3 mm.

6. Method according to claim 1 wherein said chips are formed with a thickness of the order of 0.05-0.1 mm and a length of about 0.5-2 mm.

7. Method according to claim 1 in which the comminution is carried out at a temperature below 0° C.

8. Method according to claim 1 in which said frozen block is comminuted at a temperature of about −1° to about −5° C.

9. Method according to claim 1 in which said frozen block of pancreas glands is extracted with a solvent for insulin, and insulin is recovered from said solvent.

10. Method according to claim 1 comprising planing said frozen block of pancrase glands to form said mass of chips having high surface area.

* * * * *